(12) United States Patent
Hörnig

(10) Patent No.: US 7,540,661 B2
(45) Date of Patent: Jun. 2, 2009

(54) PATIENT TABLE FOR AN X-RAY SYSTEM

(75) Inventor: Mathias Hörnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 278 days.

(21) Appl. No.: 11/478,508

(22) Filed: Jun. 29, 2006

(65) Prior Publication Data

US 2007/0003022 A1 Jan. 4, 2007

(30) Foreign Application Priority Data

Jun. 29, 2005 (DE) .................. 10 2005 030 378

(51) Int. Cl.
*A61B 6/04* (2006.01)
*A47B 7/00* (2006.01)

(52) U.S. Cl. .............. 378/209; 5/601; 5/606; 5/613

(58) Field of Classification Search ........... 378/204, 378/205, 208, 209; 5/600–602, 607, 610, 5/613–619, 621–624, 604, 606, 620
See application file for complete search history.

(56) References Cited

U.S. PATENT DOCUMENTS

| | | | | |
|---|---|---|---|---|
| 2,691,782 A * | 10/1954 | West ................ | 5/81.1 HS |
| 3,302,021 A * | 1/1967 | Hardy .............. | 378/174 |
| 3,411,766 A * | 11/1968 | Lanigan ............ | 5/619 |
| 3,766,384 A * | 10/1973 | Anderson .......... | 378/209 |
| 3,845,947 A * | 11/1974 | Lee ................. | 5/613 |
| 4,103,170 A * | 7/1978 | Spradlin ........... | 378/179 |
| 4,411,035 A * | 10/1983 | Fenwick ........... | 5/602 |
| 4,723,588 A * | 2/1988 | Ruppel ............. | 160/236 |
| 4,998,308 A * | 3/1991 | Farago ............. | 5/424 |
| 5,131,105 A * | 7/1992 | Harrawood et al. .. | 5/607 |
| 5,155,756 A * | 10/1992 | Pare et al. ........ | 378/196 |
| 5,613,254 A * | 3/1997 | Clayman et al. .... | 5/600 |
| 6,038,718 A * | 3/2000 | Pennington et al. . | 5/618 |
| 6,237,172 B1 * | 5/2001 | Morgan, Sr. ....... | 5/618 |
| 6,298,506 B1 * | 10/2001 | Heinold et al. .... | 5/613 |
| 6,421,853 B1 * | 7/2002 | Pecorelli et al. .. | 5/606 |
| 6,459,923 B1 * | 10/2002 | Plewes et al. ..... | 600/411 |
| 6,813,788 B2 * | 11/2004 | Dinkler et al. .... | 5/622 |
| 6,941,599 B2 * | 9/2005 | Zacharopoulos et al. | 5/601 |
| 6,983,501 B2 * | 1/2006 | Heimbrock et al. .. | 5/602 |
| 7,076,821 B2 * | 7/2006 | de Mooy ........... | 5/601 |
| 2002/0095730 A1 * | 7/2002 | Al-Kassim et al. .. | 5/601 |
| 2004/0101360 A1 * | 5/2004 | Schwartz et al. ... | 403/408.1 |
| 2004/0163177 A1 * | 8/2004 | Stryker et al. .... | 5/626 |
| 2005/0135560 A1 * | 6/2005 | Dafni et al. ...... | 378/101 |
| 2005/0198736 A1 * | 9/2005 | Jahrling .......... | 5/601 |
| 2007/0039101 A1 * | 2/2007 | Luginbuhl et al. .. | 5/600 |

FOREIGN PATENT DOCUMENTS

DE 3143894 A1 * 5/1983
DE 94 18 386 U1 4/1995

* cited by examiner

*Primary Examiner*—Edward J Glick
*Assistant Examiner*—Anastasia Midkiff

(57) ABSTRACT

Disclosed is a patient table for an x-ray system with a table top, the length of which can be optionally varied. The table top can be of a modular design, or can comprise a plurality of table segments or slats depending on the type of x-ray device used.

17 Claims, 3 Drawing Sheets

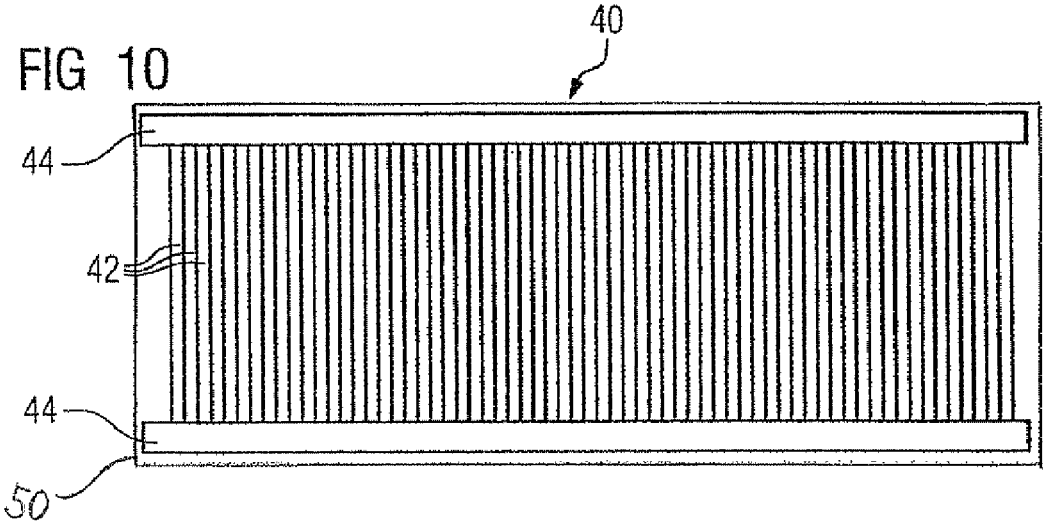
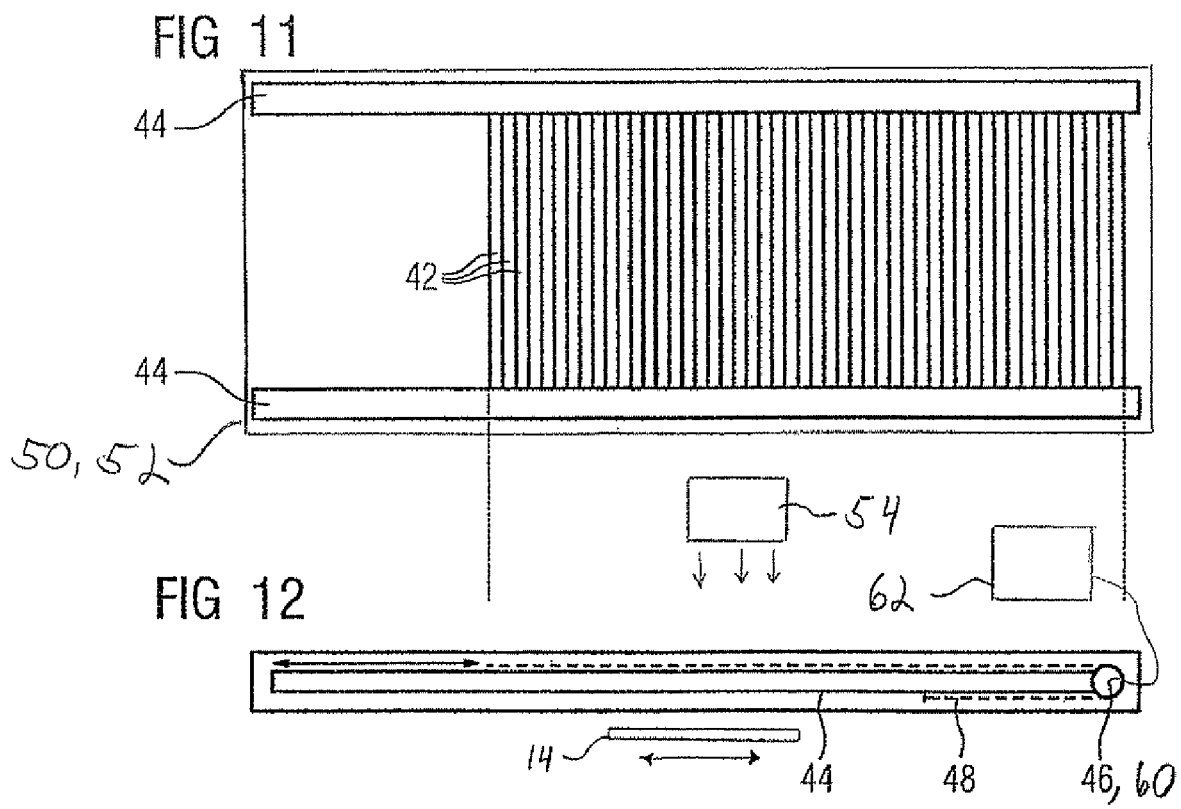

PATIENT TABLE FOR AN X-RAY SYSTEM

CROSS REFERENCE TO RELATED APPLICATIONS

This application claims priority of German application No. 10 2005 30 378.1 filed Jun. 29, 2005, which is incorporated by reference herein in its entirety.

FIELD OF THE INVENTION

The invention relates to a patient table for an x-ray system with a table top.

BACKGROUND OF THE INVENTION

X-ray systems are increasingly designed such that they cover as many clinical applications as possible with one device. Advantages of these types of universal and combined systems are the low costs and space requirements.

Applications pertaining hereto are those in which the patient is not positioned on a patient table, but is instead standing and supported by the table. Examples for this are x-ray recordings of the lung. The patient table is then brought into an upright position. In the prior art, the patient cannot get sufficiently close to the detector, as a result of the table top located in the radiation path, which results in a geometric enlargement of the image and a geometric limitation of the region to be examined. By way of example, the quality of the lung recordings is hereby restricted in that the shoulder regions (tips of the lungs) are not imaged sufficiently well. The positioning of the patient to the detector is complicated since it is not possible to fix him/her to the detector housing or to position him/her suitably. The table top gets in the way here.

An advanced solution is the so-called wall stand solution, with which the x-ray tube of a table system can be aligned to a wall, behind which the image receiver is located. This solution is complex and requires more space, thereby rendering it expensive.

Provision was also partially made to remove the entire table top. Since this is an extremely heavy load, its removal is very complex.

A fluoroscopy table with detachable parts for endoscopic applications is known from the company Hitachi.

An adjuster which can be used for instance with an x-ray table is known from DE 94 18 386 U1, with which a complex collapsible mechanism enables a wheelchair to optionally assume the function of a chair or the function of a table.

SUMMARY OF THE INVENTION

With the x-ray systems of the prior art, it is the object of the invention to provide a measure, by means of which the x-ray system retains its flexible applicability, with the recording in particular being more easily configurable in the case of an upright patient table.

This object is achieved by a patient table and by an x-ray system according to the claims.

By changing the length of the table top, regions of the patient can "be released" in a certain manner, i.e. with the said situation, such that the table top stands upright, the table top can be shortened such that the head of the patient and if necessary also the shoulders approach the x-ray detector, which is usually located below the table top and naturally behind it when in an upright position.

The table top may be made of at least two modules, of which at least one (in particular in the region of the patient head) can be optionally removed.

In contrast to a complete table top, a small module can be easily removed; however, the complete table top need not always be removed, and it is instead sufficient for the said module to release the upper body of the patient or at least the head of the patient. A module which is located in particular in the region of the patient's head (head module) is easy to carry and its removal is thus not a problem even for persons of limited strength.

The two modules are preferably interlocking and locked. This increases the stability of the patient table. By way of example, the locking of the module can be unlocked after actuating at least one bolt, such as for instance a damping spring bolt. Such a spring bolt prevents a module from being unintentionally removed.

The profiles of the two modules are also designed to interlock along the thickness direction of the table top, i.e. in the direction of the height of the table top (with a horizontal table top). This should not only increase the stability, but also essentially inhibit the flow rate of fluid. In addition, provision is made in the region of the interlocking in a module profile for a groove or notch for receiving fluid seeping through the region. In this way, the x-ray detector is hereby particularly protected against the patient's bodily fluids, which can occasionally escape during some treatments.

The table top can be formed from a plurality of table segments or slats which can be moved together in the manner of a roller blind. The length of the table top can be very well adjusted to the patient's size, i.e. the length of the table top can be varied very flexibly.

The slats can be surrounded by a solid casing, which prevents fluid from passing through the table top. Bars can be located in the solid casing, so that a sealed chamber is formed for each individual slat. The slats can be guided into a rail for maneuverability purposes and can be manufactured from carbon fiber material. Alternatively, the table segments could also be designed as hollow chambers.

The invention also relates to an x-ray system with an x-ray emitter and an x-ray detector and a patient table of the above-mentioned type located therebetween.

The patient table is to be optionally modifiable in terms of the table top length such that with shortened table top lengths, the head and if necessary the shoulders of the patient can be guided into direct contact with the x-ray detector.

Occasionally the detector is not located directly in the region of the head or, if necessary, the lungs to be imaged. Provision can be made for the x-ray detector to be moveable with shortened table top lengths. By way of example, the movement of the x-ray detector can be triggered by removing an x-ray module or by shortening the roller blind-type table top. The x-ray detector can then be moved behind the (remaining) table, such that at least one sub-area of the x-ray detector can be directly radiated by the x-ray emitter (after x-raying the patient) and the table top is no longer located in the corresponding radiation path to the x-ray detector. This measure allows a remaining interference to be stopped by means of the remaining table top.

With the above-described embodiment of the connection of second modules, which are locked, with the locking being unlockable by actuating a bolt, the bolts can be electronically released or actuated in the x-ray system according to the invention. The electronic release or actuation of the bolt can be carried out as a function of a tilting angle of the patient table. Conventional x-ray systems have sufficient data processing systems for such a control.

With the above-described embodiment of the roller blind-type patient table, the table segments can be moved by means of an electric motor 60, which is actuated via a mechanical input device 62, in particular a joystick on the x-ray system. It can also be possible for the roller blind to be automatically actuated as a function of a tilting angle of the patient table.

The above mentioned triggering of the bolt or movement of the roller blind type patient table as a function of a tilting angle of the patient table allows the patient table to be shortened only when it is upright, in other words for a lung recording for instance, whereas when the patient table is in a horizontal position, the corresponding functionality to shorten the patient table can be electronically blocked (by means of a corresponding programming of the data processing system etc.), so that the patient table is not shortened by mistake.

BRIEF DESCRIPTION OF THE DRAWINGS

Preferred embodiments of the invention are now described in more detail below with reference to the drawings, in which.

DETAILED DESCRIPTION OF THE INVENTION

Figure 1:
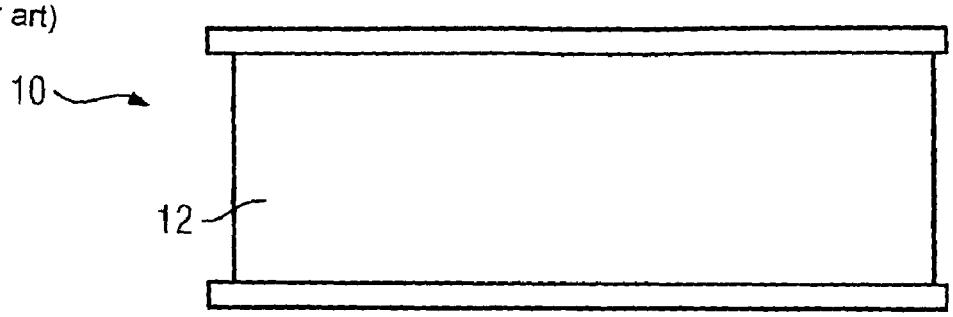
FIG. 1 shows a patient table according to the prior art.

FIG. 1 shows a patient table 10 of the prior art for an x-ray system with a stable, fixed table top 12 comprising one piece.

Figure 5:
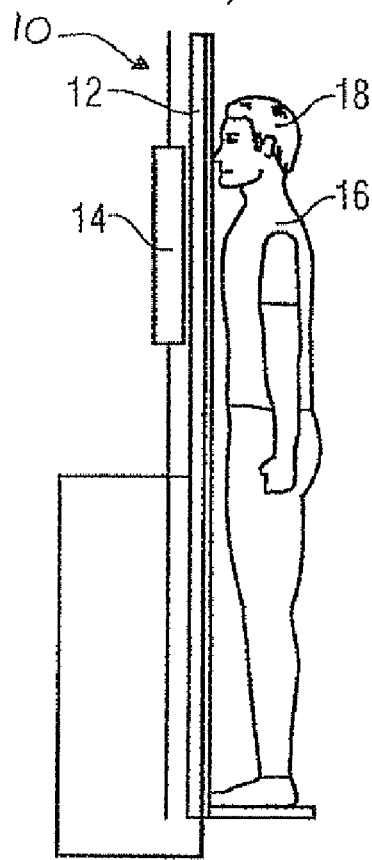
FIG. 5 illustrates an upright patient table according to the prior art.

In the prior art, the table top 12 is then in the way if the patient is to be recorded in an upright position. This is illustrated in FIG. 5. When the patient table 12 is in an upright position, the patient table interferes in the radiation path (from the x-ray emitter (54)) to the x-ray detector 14. It would be desirable for a patient 16 to move his/her head 18 as close as possible to the x-ray detector 14. Compared with the horizontal function, the table 12 has completely lost its function and in the prior art is frequently completely removed. Such a table is however very heavy.

Figure 2:
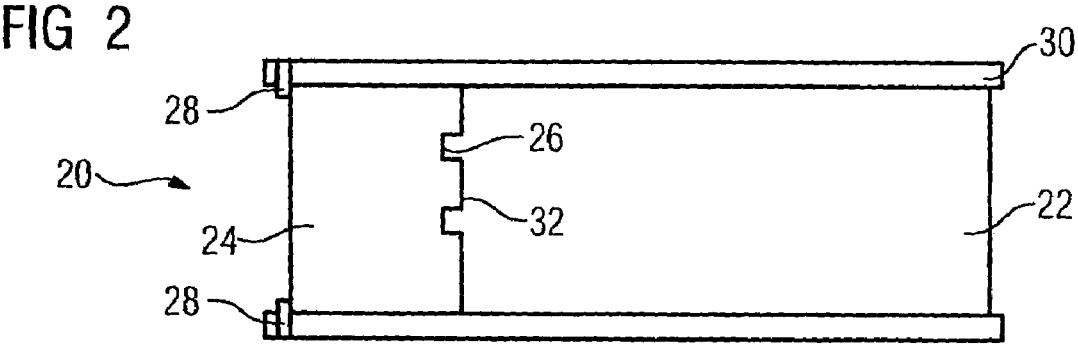
FIGS. 2 to 4 show a top view on the patient table according to a first embodiment of the invention, with the sequence of FIGS. 2 to 4 illustrating the release of a head module.

The invention provides a patient table 20, as shown in FIG. 2. The patient table 20 comprises two modules, a main table module 22 and a head module 24. The two modules interlock at their juncture by means of teeth 26 and are locked.

Figure 3:
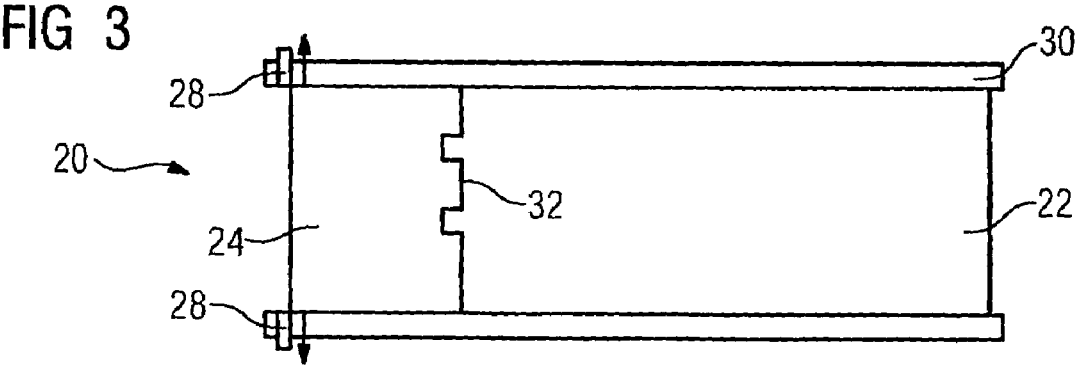
Figure 4:
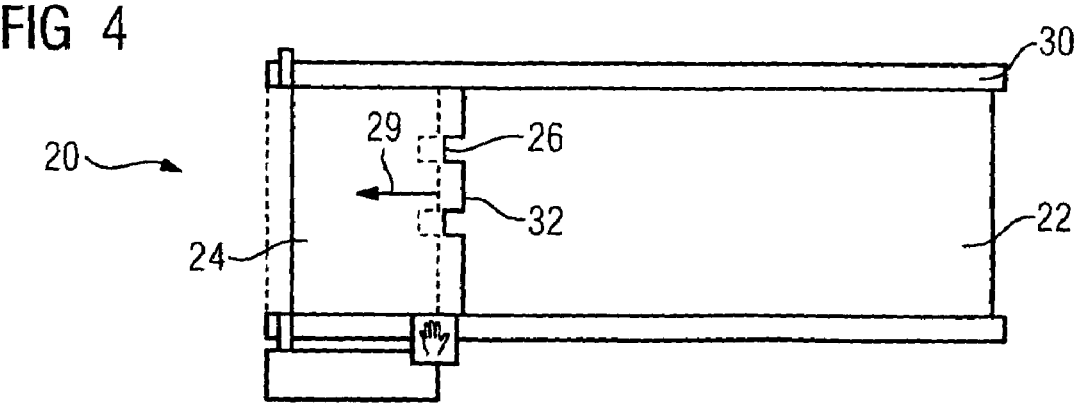

Damping spring bolts 28, which prevent the head module from being removed, are disposed on both sides of the head module 24. In FIG. 3, the damping spring bolts are forced to the side. In this situation, it is possible, as shown in FIG. 4, to move the head module 24 in the image towards the left, i.e. upwards in the upright position, (see arrow 29 and the illustration of the moved head module 24 shown with a dashed line). A lateral removal of the head module is then possible.

The damping spring bolts 28 can be electronically released or at least electronically blocked. By way of example, an electromagnet can prevent the damping spring bolts 28 from being opened and the electromagnet can only then release the damping spring bolts 28 when the patient table 20 is in an upright position.

Figure 6:
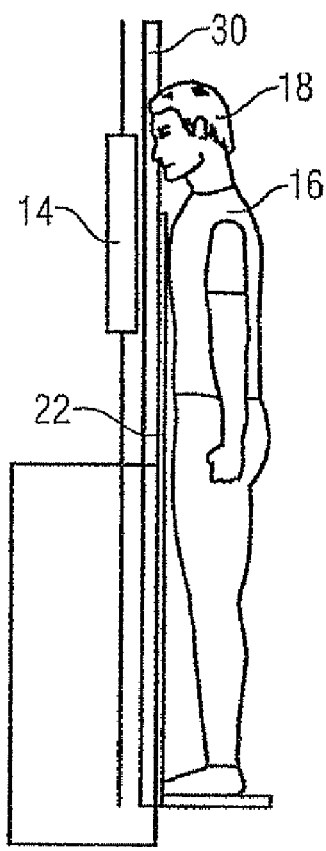
FIG. 6 shows an upright patient table according to the invention.

A shortened patient table is thus achieved according to the process shown in FIG. 2, which only comprises the main table module 22, in other words the situation illustrated in FIG. 6 is achieved. The patient 16 can move his/her head 18 freely towards the detector 14 after the head module 24 has been removed. In this way, the patient can be supported by the main table module 22, and the head thus protrudes between the frame 30 of the table 20. An improved x-ray imaging can thus be achieved.

One problem which can occur by means of the modular design of the patient table 20 is that the presence of a line of separation 32 between the main table module 22 and the head module 24 enables bodily fluids, which escape during the treatment of the patient, to seep through the patient table and finally onto the detector positioned below the table, which is not desirable.

To prevent this, the height profiles of the two modules 22 and 24 can be embodied in a suitable manner.

Figure 7:
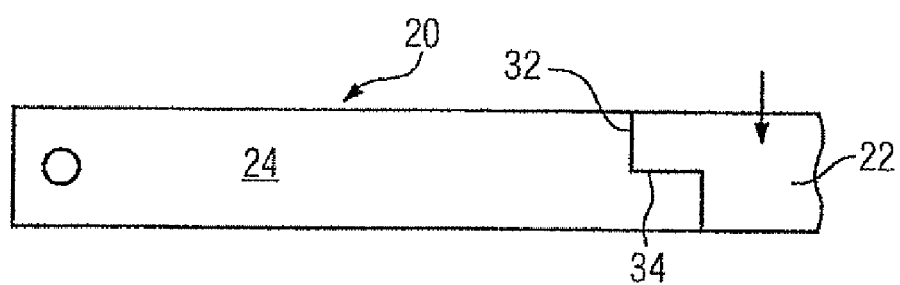
FIGS. 7 to 9 show possible side views and/or profile views of a patient table according to the invention of the type shown in FIG. 2, FIGS. 10 to 12 show a second embodiment of the patient table according to the invention, with FIG. 10 showing the patient table over the full length of the table top, FIG. 11 showing the patient table with a shortened table top and FIG. 12 showing a side view of the table according to FIG. 11.
Figure 8:
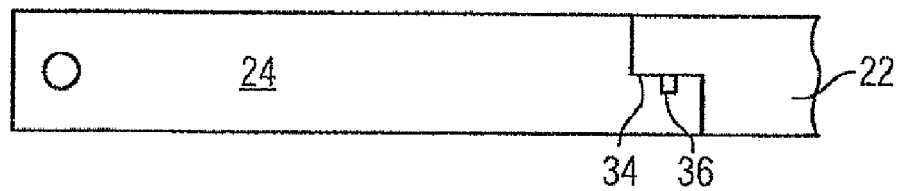
Figure 9:

FIGS. 7 to 9 show different height profiles of a table 20 according to the invention of the type as shown in FIG. 2. FIGS. 7 to 9 are thus side views of the patient table 20 according to three possible embodiments. The engagement of the main table module 22 (illustrated with a dashed line) into the head module 24 is shown. The main table module 22 comprises a region protruding somewhat at its end, i.e. features a step 34, below which the main table module regresses somewhat. To this end, the head module 24 is designed in a complementary fashion, i.e. it features a step-like protrusion in the lower region, on which the protrusion of the main table module is perfectly seated. Although a line of separation 32 in principle allows fluids to seep through, the path for the fluid around the corner is so intricate that generally it does not result in fluid seeping through.

FIG. 8 shows a preferred embodiment, in which a groove or notch 36 is provided in the step-like protrusion of the head module 24, in which groove or notch the fluid can collect, should it already have penetrated at the boundary line 32.

In the embodiment displayed in FIG. 9, a protrusion 38 protrudes out of the main table module 22 at a mid height, to which a corresponding recess in the head module 24 is precisely complementary. With the embodiment shown in FIG. 9, a high resistance to leakage is likewise ensured.

The modular design on the basis of FIGS. 2 and 4 is advantageous because it is simple and in particular existing patient table systems can be easily retooled by replacing the table top.

With this modular design, it is not possible to flexibly adjust the patient table length as a function of the size of the patient.

A second embodiment of the invention with an inventive patient table 40 serves this purpose, as shown in FIG. 10. The patient table 40 comprises a plurality of slats 42. The slats are located in a fluid-tight casing (50), in which are designed chambers for individual slats. The slats 42 are guided towards both sides of the patient table in a rail 44. As shown in FIG. 12, the rail 44 is designed to be double, i.e. the guided slats 42 can be guided around a deflection mechanism 46 and then continue in a second part of the track 44.

The patient table according to the invention thus functions according to the manner of a roller blind (with equally spaced slats). The entire number of slats 42 can be completely moved about the deflection device 46, with some of the slats, characterized in FIG. 12 with 48, being located below the other slats 42.

The slats can also be made of carbon material. The use of a roller blind-type arrangement enables the length of the table top to be essentially changed in a continuous manner, so that the table top setting can be perfectly adjusted to a specific patient and the specific recording situation. The roller blind can be adjusted by means of an electromotor, which is operated using a joystick by the operator operating the x-ray system.

Since the slats 42 do not disappear, but some of them 48 are merely located below (or, depending on the position of the patient table, behind) the other slats, the table top can be shortened up to a maximum of a half.

Instead of slats 42 in chambers, hollow chambers (52) can also be used as moveable table segments in the embodiment.

The invention claimed is:

1. A patient table for an x-ray system, comprising:
   a table top consisting of a plurality of interlocking modules, wherein
      a length of the table top is changeable and at least one of the modules is removable, and
      an interface of the interlocking modules is configured to essentially inhibit a fluid from seeping through between the interlocked modules in a region of the patient's head.

2. The patient table as claimed in claim 1, wherein the modules are unlocked by actuating a damping spring bolt.

3. The patient table as claimed in claim 1, wherein profiles of the modules along a thickness direction of the table top are interlocked with respect to each other.

4. The patient table as claimed in claim 1, wherein a groove or a notch is provided in a region of the interlocking area to receive a fluid, said groove or notch being in the region of the patient's head.

5. A patient table for an x-ray system, comprising:
   a table top consisting of a plurality of table segments, wherein
      the table segments are movable together as a roller blind so that a length of the table top is changeable, and
      the table segments form interlocking modules where the interlocking interface is configured to essentially inhibit a fluid from seeping between the interlocked modules in a region of the patient's head.

6. The patient table as claimed in claim 5, wherein the table segments are slats which are surrounded by a solid casing, the solid casing preventing a fluid from passing through the table top.

7. The patient table as claimed in claim 5, wherein the table segments are guided in a rail.

8. The patient table as claimed in claim 5, wherein the table segments are manufactured from a carbon fiber material.

9. The patient table as claimed in claim 5, wherein the table segments are hollow chambers.

10. An x-ray system for taking an x-ray image of a patient, comprising:
    an x-ray emitter;
    an x-ray detector; and
    a patient table having a table top with a changeable length, wherein
       the table top comprises a plurality of interlocking modules where the interlocking interface is configured to essentially inhibit a fluid from seeping between the modules in a region of the patient's head.

11. The x-ray system as claimed in claim 10, wherein a head of the patient is guided into a direct contact with the x-ray detector with the table top in a shortened length position.

12. The x-ray system as claimed in claim 10, wherein shoulders of the patient are guided into a direct contact with the x-ray detector with the table top in a shortened length position.

13. The x-ray system as claimed in claim 10, wherein with the table top in a shortened length position, the x-ray detector is moved so that the table top is not located in a radiation path of the x-ray emitter in a partial region of the x-ray detector.

14. The x-ray system as claimed in claim 10,
    wherein the interlocked modules are electronically released or actuated by a bolt.

15. The x-ray system as claimed in claim 14, wherein the electronic release or actuation is carried out as a function of a tilting angle of the patient table.

16. The x-ray system as claimed in claim 10,
    wherein the patient table consists of a plurality of table segments, and
    wherein the table segments are moveable by an electromotor which is actuated by a mechanical input device, or are automatically actuated as a function of a tilting angle of the patient table.

17. The x-ray system as claimed in claim 16, wherein the mechanical input device is a joystick.

* * * * *